(12) United States Patent
Taghavi et al.

(10) Patent No.: US 11,344,687 B2
(45) Date of Patent: May 31, 2022

(54) EXPANDABLE SPACERS, VALVED HOLDING CHAMBERS AND FACE MASKS FOR INHALERS

(71) Applicants: Pedram Taghavi, Coquitlam (CA); Siamak Arzanpour, North Vancouver (CA); Shahab Azimi, Burnaby (CA)

(72) Inventors: Pedram Taghavi, Coquitlam (CA); Shahab Azimi, Burnaby (CA); Siamak Arzanpour, North Vancouver (CA); Fereidoon Rashidi, Port Moody (CA)

(73) Assignee: Pedram Taghavi, Coquitlam (CA)

( * ) Notice: Subject to any disclaimer, the term of this patent is extended or adjusted under 35 U.S.C. 154(b) by 280 days.

(21) Appl. No.: 16/422,932

(22) Filed: May 24, 2019

(65) Prior Publication Data

US 2019/0358415 A1 Nov. 28, 2019

Related U.S. Application Data

(60) Provisional application No. 62/677,063, filed on May 28, 2018.

(51) Int. Cl.
*A61M 15/00* (2006.01)

(52) U.S. Cl.
CPC ...... *A61M 15/0088* (2014.02); *A61M 15/002* (2014.02); *A61M 15/009* (2013.01); *A61M 15/0021* (2014.02)

(58) Field of Classification Search
CPC ...... A61M 11/00; A61M 11/02; A61M 11/06; A61M 11/08; A61M 15/00–0001; A61M 15/0013; A61M 15/0016; A61M 15/0018; A61M 15/002–0021; A61M 15/0086–009

See application file for complete search history.

(56) References Cited

U.S. PATENT DOCUMENTS

| | | | |
|---|---|---|---|
| 5,121,745 A * | 6/1992 | Israel | A61M 16/06 128/202.28 |
| 5,305,739 A | 4/1994 | Gray | |
| 2001/0035182 A1 * | 11/2001 | Rubin | A61M 15/00 128/200.23 |
| 2002/0069869 A1 | 6/2002 | Farmer | |
| 2002/0073934 A1 | 6/2002 | Barney et al. | |
| 2002/0091344 A1 * | 7/2002 | Thomas | A61H 9/0078 601/148 |

(Continued)

FOREIGN PATENT DOCUMENTS

| CA | 3044202 A1 | 11/2019 |
|---|---|---|
| GB | 2412325 B | 2/2006 |

OTHER PUBLICATIONS

Canadian Patent Office Examination report dated Jun. 30, 2020.

(Continued)

*Primary Examiner* — Rachel T Sippel

(57) ABSTRACT

A device, called expandable spacer, for improving the efficacy of drug delivery in metered dose inhalers is described. The device has a body made of flexible (might be expandable) material. It can shrink in size when it is not in use and can go back to its normal shape and size when it is used. The device further comprises a valve (can be one way valve) that helps the drug to be maintained inside the spacer's cavity and opens during inhalation and closes during exhalation.

10 Claims, 7 Drawing Sheets

(56) References Cited

U.S. PATENT DOCUMENTS

| | | | |
|---|---|---|---|
| 2005/0172955 A1* | 8/2005 | Sundaram | A61M 15/0016 |
| | | | 128/200.23 |
| 2007/0283954 A1 | 12/2007 | Dhuper | |
| 2008/0035143 A1* | 2/2008 | Sievers | A61M 11/008 |
| | | | 128/203.12 |
| 2011/0132359 A1* | 6/2011 | Poree | A61M 15/0018 |
| | | | 128/203.21 |
| 2013/0276781 A1* | 10/2013 | Steelman | A61M 15/0023 |
| | | | 128/203.12 |
| 2018/0116418 A1* | 5/2018 | Shakal | F16K 31/0689 |
| 2021/0001064 A1* | 1/2021 | Clements | A61M 15/0088 |
| 2021/0001065 A1* | 1/2021 | Clements | A61M 15/0021 |

OTHER PUBLICATIONS

Response submitted by the applicant on Mar. 14, 2021 regarding Canadian Patent Office Examination report dated Jun. 30, 2020.
Canadian Patent Office Examination report dated May 20, 2021.

\* cited by examiner

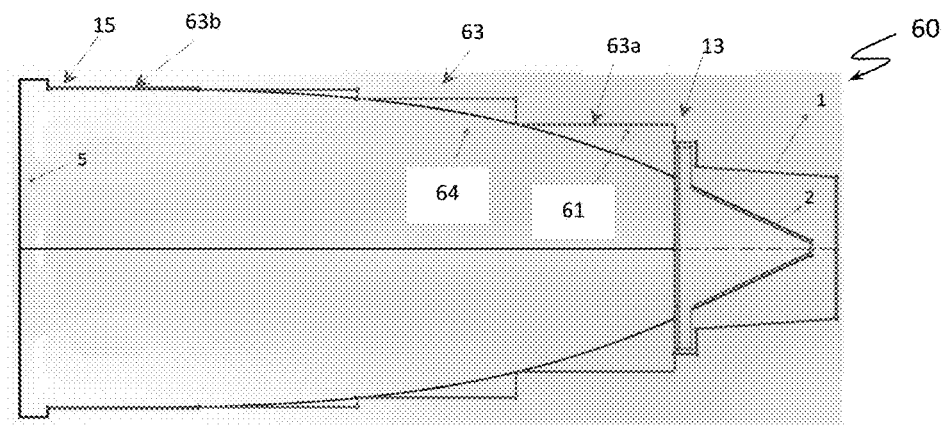
FIG. 6A
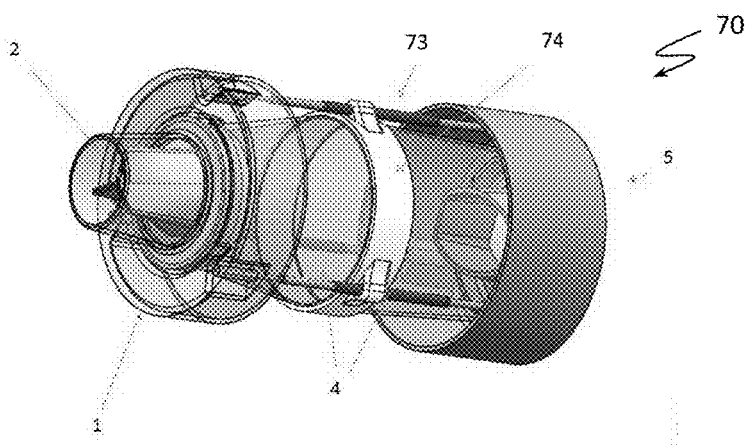
FIG. 7A
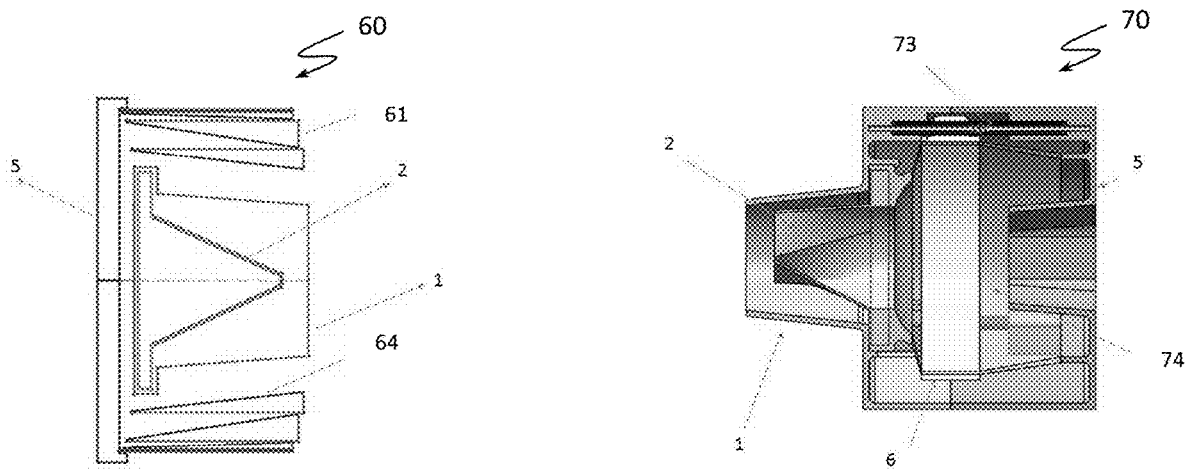
FIG. 6B
FIG. 7B

EXPANDABLE SPACERS, VALVED HOLDING CHAMBERS AND FACE MASKS FOR INHALERS

FIELD OF INVENTION

This invention relates generally to spacers, valved holding chambers and their accessories including but not limited to face masks for inhalers, and more particular to spacers and valved holding chambers that are expandable when in use and collapsible to a smaller size when not in use.

BACKGROUND OF INVENTION

Unless otherwise indicated herein, the materials described in this section are not prior art to the claims in this application and are not admitted to be prior art by inclusion in this section.

Asthma and Chronic obstructive pulmonary disease (COPD) are the two major airway diseases that globally affect nearly 500 million people. Pressurized metered-dose inhaler (pMDI) is a patient-administered device that allows a prescribed amount of medication to be administered as an inhaled aerosol to improve delivery of the medication. Usually the pMDI comprises a medicament-containing pressurized canister containing a mixture of an active medication and a propellant. In order to actuate the inhaler, the user applies a compressive force to a closed end of the canister to actuate a metering valve and cause a metered quantity of the medication and the propellant to be expelled through the valve stem into a mouthpiece of the inhaler, such that a user inhaling through the outlet of the inhaler will receive a prescribed dose of the medication. Although pMDI is the preferred device for drug delivery, poor synchronization between its actuation and drug inhalation by the user limits the effectiveness of pMDI. In addition a high proportion of the medication can get deposited in a mouth and throat of the user, where it can lead to irritation and mild infections. Valved Holding Chambers (VHC) or spacers are add-on accessory devices that have been developed to overcome those problems. VHC or spacer is a long tube that slows the delivery of medication from the pMDI. Instead of direct inhalation, the VHC is attached to the pMDI so that patients have time to inhale laminar flow of medication in multiple inspirations without worry about the need for synchronization. Moreover, larger particles that are normally absorbed in the user's upper airways, will impact a wall of the chamber and will deposit in the VHC body. Clinical and laboratory tests demonstrate that the efficacy of drug delivery using pMDI together with VHC is comparable to that of nebulizers. Despite being strongly recommended in clinical guidelines, only a very small portion of patients use VHCs mainly because of their obtrusiveness, bulkiness and cost. Such pMDI are less portable because the VHC takes up extra space in a purse or a bag. Although several small, foldable and compact VHC designs have been introduced, their low efficacy has prevented their widespread adoption. The present invention overcomes the limitations of the prior art by developing VHCs that are pocketable and can be compressed to fit inside a pMDI package and can expand to the same size and shape of a original high efficacy VHCs and spacers.

SUMMARY OF THE INVENTION

In one aspect a collapsible spacer is provided. The spacer comprises an outlet port adapted to be brought in communication with an oral cavity of a user and a body that has a first end connected to the outlet, a second end configured to be connectable to an inhaler and a wall extending between the first end and the second end. The wall comprises a collapsible body structure defining an outer wall of the body and an elastic body structure defining an inner wall of the body. When the spacer is in an extended position the collapsible body structure has sufficient rigidity to keep a predetermined shape and integrity of the spacer and the elastic body structure is entirely stretched defining a smooth inner wall of the spacer. Upon a force is applied to the collapsible body structure it collapses to a smaller size.

In one aspect the collapsible body structure is a foam-like structure and the elastic body structure is attached to the foam-like structure at least at two points. The collapsible body structure can be a foam spring or a foam cage-like frame.

In another aspect, the collapsible spacer is a spring.

In yet another aspect, the collapsible body structure comprises a plurality of O-rings space apart one from another. Each of the O-rings is attached to the elastic body structure.

In one aspect, the collapsible body structure comprises a slidable solid body having a multiple solid compartments. A compartment at the second end of the body has a biggest diameter and a compartment at the first end has a smallest compartment. The multiple compartments are configured to slide one into the other when in the collapsed position. The elastic body structure is attached to each of the compartments to at least one point.

In another aspect, the collapsible body structure comprises an annular ring and a plurality of the telescopic rods connected to the annular ring. The elastic structure is connected to the annular ring.

In yet another aspect, the collapsible spacer further comprises an inflatable system having a pump with a valve and a nozzle. The collapsible body structure has a wall defining a closed inner cavity of the collapsible body structure and an inlet port defined as a communication port with the inner cavity of the collapsible structure. The inlet port has a removable cap and the nozzle of the inflatable system is insertable into the inlet port when the cap is removed to inflate the collapsible body structure when the spacer is in the extended position. The elastic body structure being attached to the collapsible structure at least at two points.

In another aspect, the collapsible body structure and the elastic body structure each are attached to the first and the second end of the body and are spaced apart one from another defining a closed annular cavity formed between the inner wall and the outer wall of the body. An inlet port having a removable cap is configured as communication port with the annular cavity. The nozzle of the inflatable system is inserted into the inlet port when the cap is removed to inflate the spacer when it is in the extended position.

In one aspect, a collapsible face mask is attached at the outlet of the spacer. The face mask has a collapsible outside wall and an elastic inner wall.

In one aspect, an inhaler-based delivery system is provided. The system comprises an inhaler configured to discharge an aerosolized medication and a collapsible spacer connected thereto. The inhaler has an exit port. The spacer has an outlet port and a body with a first end connected to the outlet, a second end connectable to the exit port of the inhaler and a wall extending between the first end and the second end. The wall comprises a collapsible body structure defining an outer wall and an elastic body structure defining an inner wall of the body.

In another aspect, an inhaler-based delivery kit is provided. The kit comprises a package that includes an inhaler with an exit port and containing a substance for delivery and a collapsible spacer configured to be attachable to the exit port of the inhaler when the inhaler is in use.

In yet another aspect, a method of delivering a medication to a user is provided. The method comprises connecting a collapsible spacer to an exit port of an inhaler; erecting the collapsible spacer to its extended position; actuating the inhaler so that the medication flows through the exit port into the spacer; and inhaling the medication in the spacer through the outlet port.

In addition to the aspects and embodiments described above, further aspects and embodiments will become apparent by reference to the drawings and study of the following detailed description.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure. Sizes and relative positions of elements in the drawings are not necessarily drawn to scale. For example, the shapes of various elements and angles are not drawn to scale, and some of these elements are arbitrarily enlarged and positioned to improve drawing legibility.

FIG. 6A is a cross section side view of a spacer with a slideable body structure in extended position according to another embodiment of the present invention.

FIG. 6B is a cross sectional side view of the slideable body structure of the spacer of FIG. 6A in a collapsed position.

FIG. 7A is a perspective view of a spacer with telescopic body in extended position according to another embodiment of the present invention.

FIG. 7B is a perspective view of the telescopic spacer of FIG. 7A in a collapsed position when the spacer is not in use.

DETAILED DESCRIPTION OF SPECIFIC EMBODIMENTS

The present invention describes spacers or valved holding chambers that can be used with any type of inhaler that is collapsible when not in use and extendable to a full size when in use. The spacers can be easily compressed multiple times with no electrostatic charges, and can be recyclable, washable and carried easily together with the inhaler. Within this document spacers and valved holding chambers are used interchangeably and mean aerosol-holding chambers and add-on spacing devices that are used for slow and efficient delivery of medication from inhalers such as for example a pressurized metered-dose inhaler (pMDI).

Figure 1A:
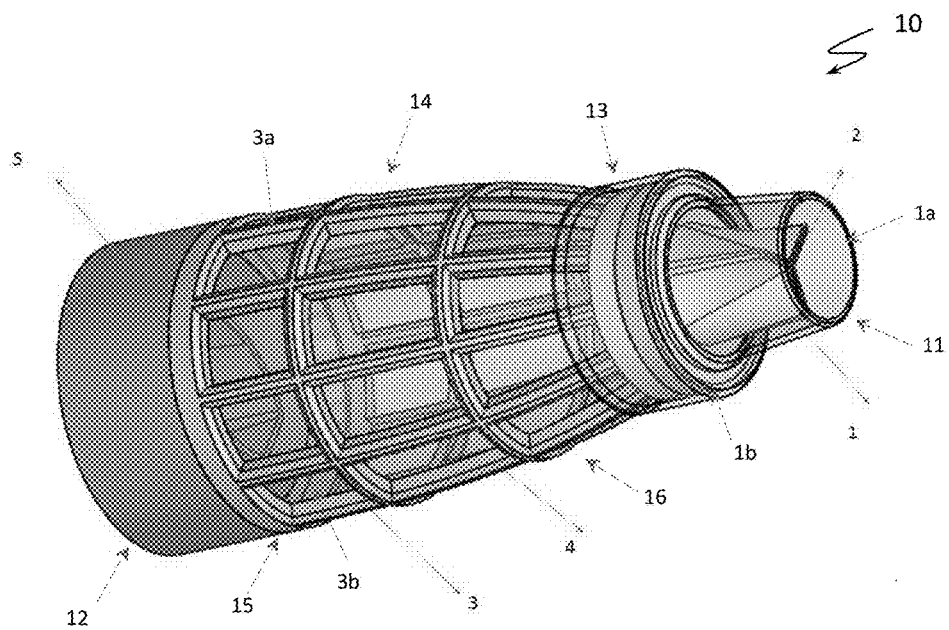
FIG. 1A is a perspective view of a spacer with a foam cage compressible body structure according to one embodiment of the present invention.

FIG. 1A shows one embodiment of a spacer 10 that can be add-on to an inhaler (not shown), such as pMDI for delivery of a prescribed amount of a medication. The spacer comprises a first end 11, a second end 12 and a body 14. A mouth piece 1 is mounted at the first end 11 so that it can be used as an inhalation outlet through which the medication or any other substance is delivered to the user. The mouth piece 1 can envelop a valve 2 that can be a one-way valve so that a medication can pass through the valve into the mouth piece during inhaling breaths of the user but would prevent any gases and/or particles going through the valve into the body 14 and from the user into the body 14 during exhaling breaths of the user. The mouth piece 1 has an outlet end 1a that is open and a distal end 1b that is connected to the valve 2 and the body 14. The body 14 comprises a first end 13, a second end 15 and a wall 16 extending between the first and the second ends 13, 15 defining the inner cavity of the spacer 10. The wall 16 comprises a collapsible body structure 3 that forms an outer surface (wall) of the wall 16 of and an elastic body structure 4 that forms in inner surface (wall). The elastic body structure 4 as defined herein means a structure that is elastic, stretchable, foldable or flexible. For example, the collapsible body structure 3 can be made of a foam or a compressible rubber. In the illustrated example the collapsible structure is a compressible element that is shaped as a cage with foam frame 3a and cells/windows 3b. The collapsible body structure 3 defines the shape and size of the spacer 10 when in its expanded position (as presented in FIG. 1A) and is used to increase the shape integrity and durability. The elastic body structure 4 can be an elastic membrane or cover that is integrated with the collapsible body structure 3 such that the elastic membrane defines the inner surface of the wall 16. So, the elastic body structure 4 defines the inner surface of the wall 16 while the collapsible structure 3 defines the outer surface of the wall 16. The elastic body structure 4 can be attached to a bottom of the frame 3a along the entire surface of the frame 3a or it can be attached to the frame 3a at multiple points such that when the spacer 10 is in the expanded position the elastic membrane is fully stretched forming a smooth inner surface with a desired predetermined shape and geometry profile necessary fir efficient medicine delivery. The elastic membrane can be attached to the compressible cage by gluing it or any other connecting method. In one implementation, the collapsible structure 3 is spaced apart from the elastic structure 4 defining an annular cavity between the inner surface and the outer surface of the wall 16. In any implementation, the elastic structure 4 needs to ensure that the inter wall of the spacer 10 has the required medical standards such as for example, biomedical grade, smooth, anti-electrostatic, hydrophobic/hydrophilic, durable, recyclable, washable etc.

The spacer 10 can further comprises a connector 5 configured to connect the spacer 10 to the inhaler. The connector 5 can be an MDI piece configured to connect the spacer 10 to the pMDI. The connector 5 can be integrated part of the spacer 10 or it can be detachable from the body 14 for cleaning purposes. In one implementation, the connector 5 can be integrated with the inhaler (see FIG. 2B) and the spacer 10 can be attached to it when the inhaler is in use and detached when the inhaler is not in use.

Figure 1B:
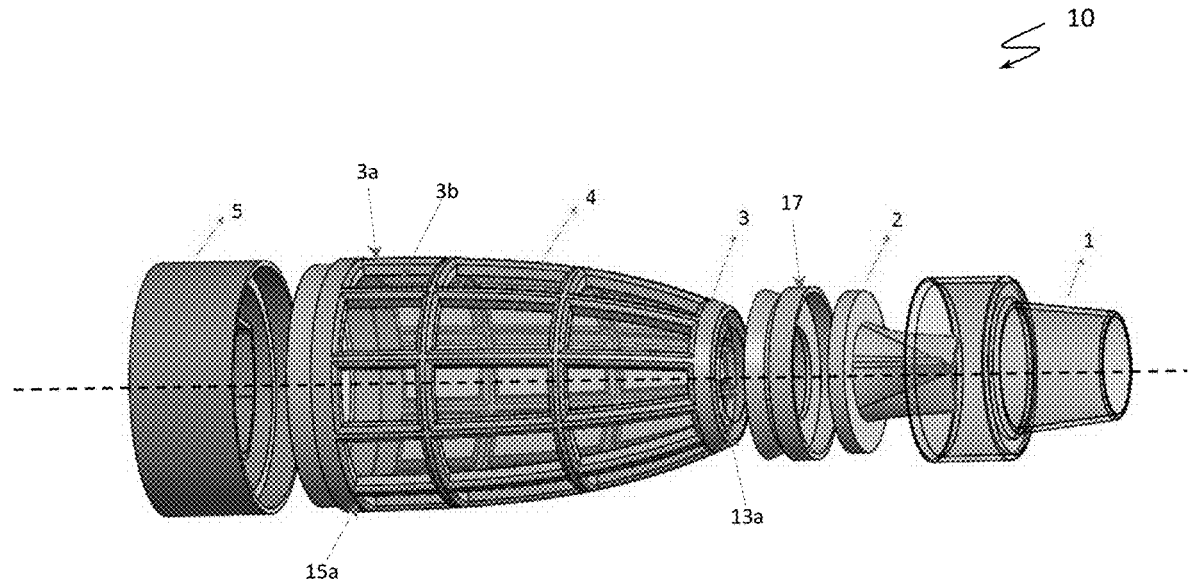
FIG. 1B is an exploded view of the spacer shown in FIG. 1A.

FIG. 1B is an exploded view of the spacer 10 showing its elements. An adapter 17 is configured to connect the valve 2 and the mouth piece 1 with the first end 13 of the body 14. The first end 13 can comprise a rigid annular element 13*a* and the second end 15 can have a rigid annular element 15*a*. The second end 15 of the body 14 can be adapted to connect to the connector 5. For example, the second end 15 can have treads so that the connector 5 can be screw to the body 14. This is for exemplary purposes only and the body 14 and the connector 5 can be connected using any suitable connecting means, i.e. snap fit, without departing from the scope of the invention.

The spacer 10 can be compressed or can collapse to a very small shape and can be stored in a packaging together with the inhaler. Upon release the spacer 10 will retain its original shape and can be immediately used by the user. Upon use, the user can clean the spacer 10 and then compress it again, store it or carry it with him/her for more convenience.

Figure 2A:
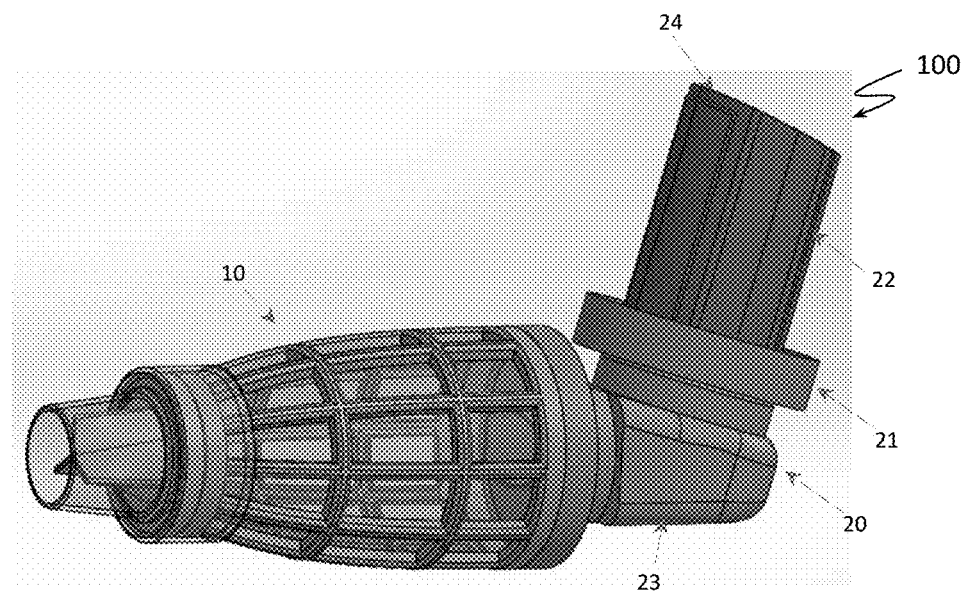
FIG. 2A is a perspective view of a metered-dose inhaler with a spacer connected thereon when the inhaler is in use.
Figure 2B:
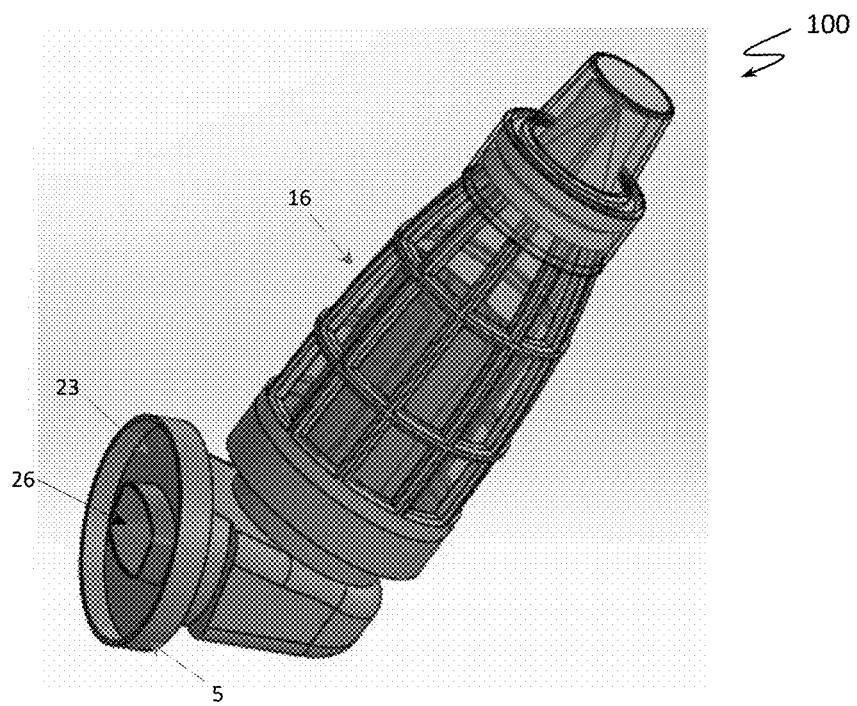
FIG. 2B is a perspective view of a metered-dose inhaler with a spacer when the inhaler is not in use.

FIG. 2A shows an inhaler-based delivery system 100 having the spacer 10 connected to an inhaler 20 when the system 100 is ready to use. The inhaler 20 can be any known inhaler with a canister 22 that contains the medication or material for delivery through such inhaler, an actuator 24 formed at a top of the canister 22 and a valve (not shown) that is opened when the actuator 24 is pressed initiating flow of the medication from the canister 22 through the valve into the inner cavity of the spacer 10. As shown in FIG. 2A, the spacer 10 is connected to a mouth piece 23 of the inhaler 20. A nozzle (exit port) 26 is used to deliver the medication from the canister 22 into the spacer 10. The mouth piece 23 can be designed to include a seat 21 adapted to receive the canister 22 of the inhaler 20. The seat 21 also includes a connector (similar to the connector 5 of FIGS. 1A, 1B) so that when the inhaler 20 is not in use the spacer 10 can be disconnected from the mouth piece 23 of the inhaler and can be mounted over the canister 22 (FIG. 2B) as a cap (rigid spacer body). In one implementation, when the spacer 10 is disconnected from the inhaler 20 it can be compressed and stored in a separate package designed for holding the spacer in its compressed state. As can be noticed in FIG. 2B, the connector 5 is integral part of the mouth piece 23 and is not part of the spacer 10. The rigid or collapsible/expandable spacer body made according to any types of mechanisms explained herein can be used as an add-on cap to the inhaler 20. The user can remove this add-on cap (spacer 10) from the MDI and attach it to the mouth piece 23 when the inhaler is in use (see FIG. 2A).

Figure 3:
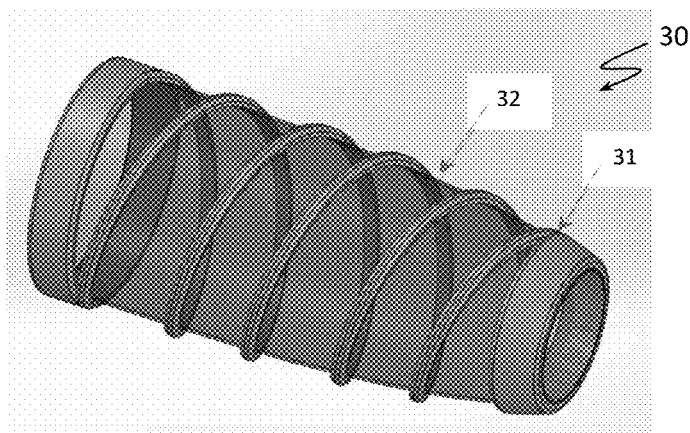
FIG. 3 is a perspective view of a spacer body with a foam spiral body structure according to another embodiment of the present invention.

The system 100 can comprise a spacer 10 that can have any given shape and structure made of a material that has a very high compressibility capability. FIG. 3 shows a spacer 30 with a collapsible body structure 31 that is designed as a spiral made of foam or any other compressible material. The collapsible body structure 31 has sufficient rigidity to keep a predetermined shape and integrity of the spacer 30 when in its extended position. An elastic body structure 32 is entirely stretched defining a smooth inner surface/wall of the spacer 30 when the spacer 30 is in extended position. So, the wall 16 of the spacer 30 has collapsible foam like made spiral 31 as an outer structure and an elastic membrane 32 as an inner wall/surface. Upon a force is applied to the collapsible body structure 31, for example the user press the spacer 30, the collapsible body structure 31 collapses to a smaller size and the elastic body structure 32 folds in multiple pleats.

The material for the collapsible body structure of the spacer is not limited to foam (open/closed cell) and can be for example a spring (FIG. 4), or can be made of electro or thermal activated materials. The material can be shaped during the manufacturing process or after it is made as a bulk to get the shape of interest. For complicated shapes and geometries the final structure can also be made by assembling sections of the device that are manufactured separately. The hybrid of several expandable materials can also be used to benefit from the characteristic of a particular material in the overall structure. For instance, a hybrid of spring with foam, spring with rubber or any other elastic/non-elastic material can be used for making the collapsible body structure 3, 31. Depending on the overall design the material can be selected as bio-grade or industrial material with proper safety consideration such as covers and coatings. The elastic body structure 4, 32 can be elastic, foldable, deformable, retractable, sliding or other possible capabilities of needs aligned with the collapsible body structure 3, 31 of the spacer 10, 30. In one embodiment, the elastic body structure 4, 32 can comprise an elastic membrane that is integrated with an expandable or non-expandable (flexible) material of the elastic body structure 4, 32.

Figure 4:
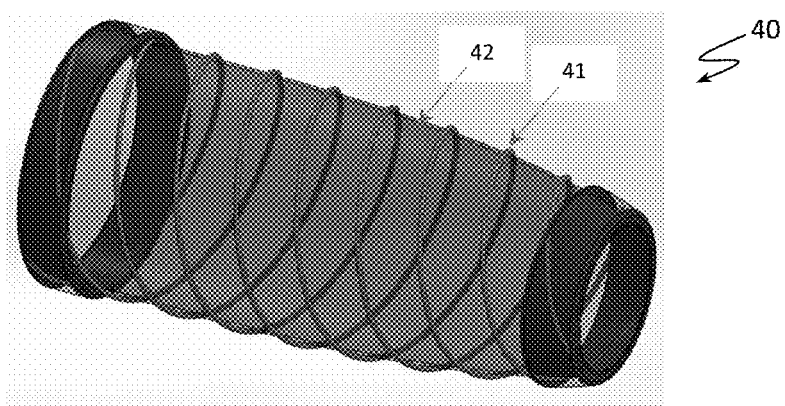
FIG. 4 is a perspective view of a spacer body with a spring body structure according to yet another embodiment of the present invention.

FIG. 4 illustrates another embodiment of a spacer 40 where the collapsible body structure is designed as a spring 41. The spring 41 forms the outer surface (skeleton) of the spacer 40 while the elastic structure forms the inner wall of the spacer 40. The elastic body structure 42 is similar to the elastic structure 4, 32 described herein above with respect to FIGS. 1 and 3. The spring 41 can be made of any suitable metal.

Figure 5:
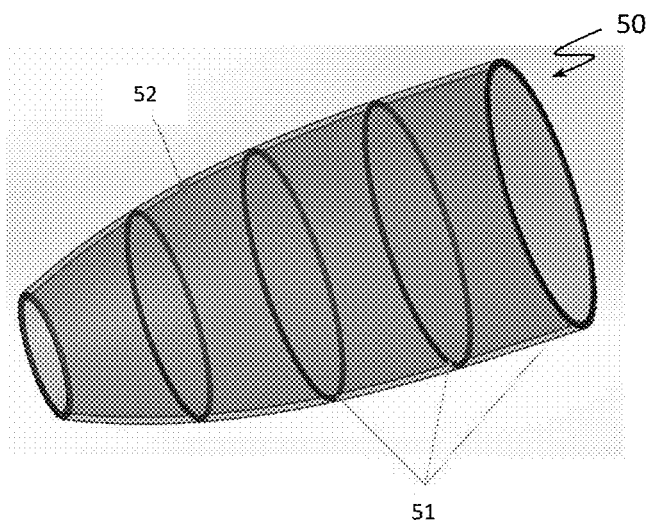
FIG. 5 is a perspective view of a spacer body with O-rings body structure according to another embodiment of the present invention.

FIG. 5 shows another embodiment of a spacer 50 that comprises a plurality of O-rings to form the outer surface/wall (e.g. skeleton) of the spacer 50 to improve the shape and integrity of a collapsible body structure 51. An elastic body structure 52 is made of some expandable or non-expandable (flexible) material (with/without cover or coating) and the O-rings 51 are placed over it to preserve the shape of the spacer 50 after its expansion. Each of the O-rings 51 is attached to the elastic structure 52 to form the body of the spacer 50.

FIG. 6A illustrates another embodiment of a spacer, such as a slideable spacer 60 having a body that comprises a multiple solid compartments 63 defining an outside sliceable solid wall 61. The multiple solid compartments 63 are designed so that the compartment 63*b* at the second end 15 of the body has the biggest diameter while the compartment 63*a* at the first end 13 has the smallest diameter so that when the spacer 60 is in its collapsed position each of the compartments slide one into the next one. An elastic membrane 64 is placed inside the slideable solid wall 61 so that the membrane 61 is attached to each of the compartments 63 at least at one point. The entire body 14 is attached to the first end 11 of the spacer 60 comprising the mouth piece 1 and the one way valve 2. The solid compartments 63 can be any material that complies with the design requirements of spacers including but not limited to metal, solid and flexible plastics as well as rubber.

FIG. 6B shows the cross section of the spacer 6A when the compartments 63 slide one into another collapsing the body 14 to its smallest size, when the spacer 60 is not in use.

FIG. 7A shows another embodiment of a spacer 70 which comprises a plurality of telescopic rods 73 connected to an annular ring 74. The telescopic rods 73 and the annular ring 74 are used to help the body of the spacer 70 to retain its shape when in an expanded position. The elastic structure 4 is attached to the annular ring 74 so that when the rods are extended it stretch defining the inner wall of the spacer 70 and when the rods 73 are collapsed one into the other the elastic membrane folds therein.

FIG. 7B illustrates the spacer 70 when the telescopic rods 73 slide inside each other so that the spacer 70 is compressed to its minimum size when it is not in use.

The integration of the solid/elastic components to the expandable part can be done by including the solid/elastic components in the mold of the expandable part during or after the expandable part is made. Also, depending on the final design, the solid/elastic parts can deform to the required shape together with the expandable material or be disconnected and separately handled.

Figure 8A:
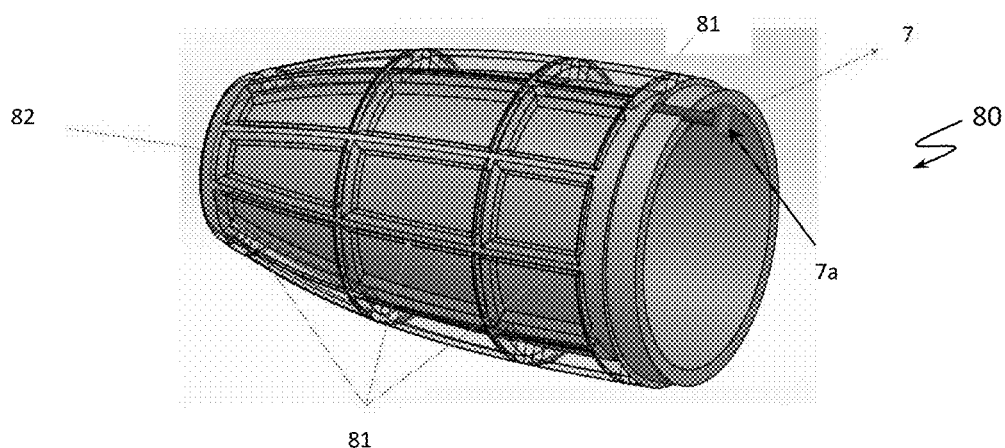
FIG. 8A is a perspective view of a caged structure inflatable spacer with a flexible inner membrane according to another embodiment of the present invention.
Figure 8B:
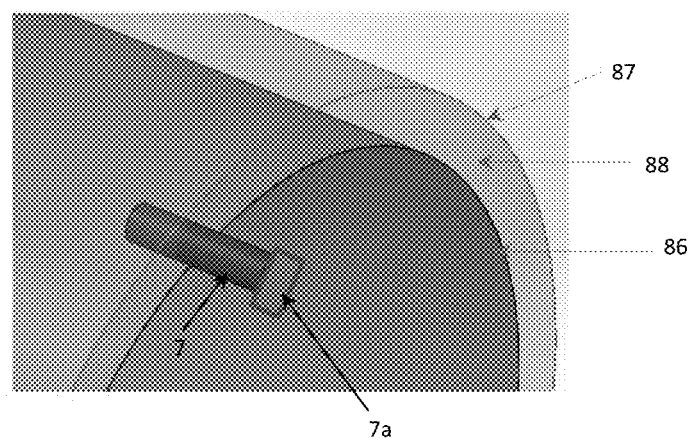
FIG. 8B is a perspective view of another embodiment of inflatable spacer showing the inflation conduit.

In one implementation, the collapsible spacer of the present invention can have an inflatable structure (see FIGS. 8A, 8B). The inflation mechanism can be manual, automated or self-inflating. The material of the inflatable structure doesn't need to be stretchable. It only needs to keep the air inside it to create the shape of the spacer.

FIG. 8A shows an embodiment of an inflatable spacer 80 with a cage shaped inflatable structure 81. The inflatable structure 81 can comprise a configuration of cells of any shape including but not limited to triangle, square, rectangle, pentagon, hexagon, etc. The inflatable structure 81 can be a network of connected tubes that can be inflated by air or any other gas to get the spacer 80 in its expanded position. In one implementation, the inflatable structure 81 can be a network of self-inflated materials. So, the inflatable structure 81 serves as an outer wall of the spacer's body and can be integrated with an elastic body structure 82. The elastic body structure 82 is similar to the elastic structure described herein above with respect to FIGS. 1, 3, 4, 5, 6 and 7 and can be attached to the inflatable structure 81 to at least one or more points. So, the collapsible body structure is actually an inflatable structure 81 that has a wall defining a closed inner cavity of such inflatable body structure 81 and an inlet port 7 as a communication port with the inner cavity of the collapsible structure. The inflatable structure 81 can be inflated through the inlet port 7 that can be a tube, pipe or any other type of conduit. A cap 7a can be provided to close the port 7 once the inflatable spacer is in the extended position. In one embodiment the outer wall (the inflatable structure 81) can be made of a flexible material (that can be stretchable) and the inner wall (the elastic body structure 82) can be made of a flexible material (that is not necessarily stretchable).

FIG. 8B shows another embodiment of an inflatable spacer 80 with a body that is entirely inflatable. The material of the inflatable structure doesn't need to be stretchable. It only needs to keep the air inside to create the shape of the spacer. The inflation mechanism can be manual, automated or self-inflating etc. So, the body 14 of the spacer 80 can be made of the inner wall 86 that is attached to the first end 13 of the body and to the second end 15 at the other, opposite side. The outer wall 87 is also attached to the first end 13 of the body and at the second end 15 at the other, opposite side so that the inner and the outer walls of the body are spaced apart one from another defining a closed annular cavity 88 formed between the inner wall 86 and the outer wall 87 of the spacer's body. An inlet port 7 having a removable cap 7a is configured as communication port with the annular cavity 88.

Figure 8C:
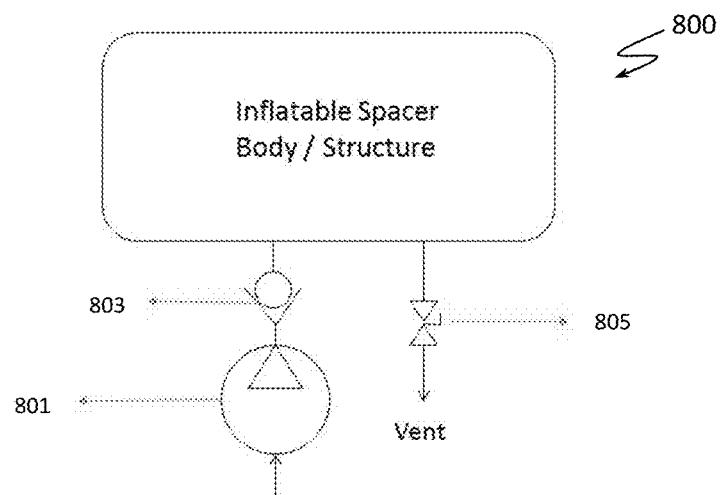
FIG. 8C is a schematic view of the inflation system used with an inflatable spacer.
Figure 9A:
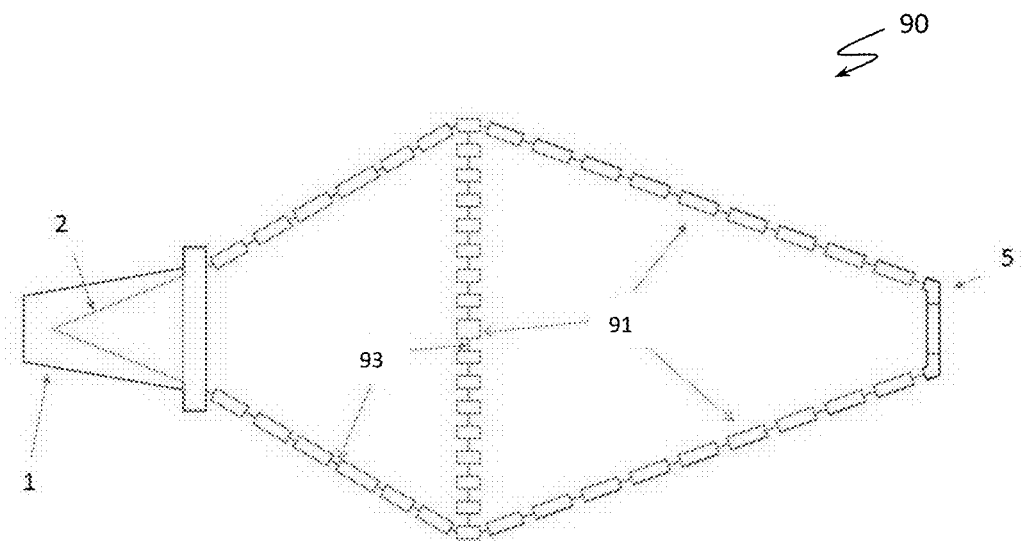
FIG. 9A is a cross-sectional side view of a foldable spacer according to an embodiment of the invention in an expanded position.
Figure 9B:
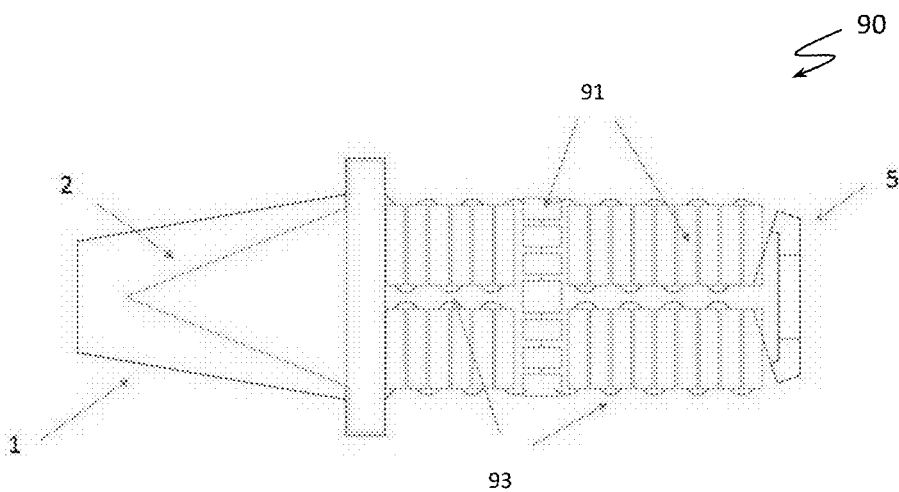
FIG. 9B is a cross-sectional side view of the foldable spacer of FIG. 9A in a collapsed position.
Figure 10A:
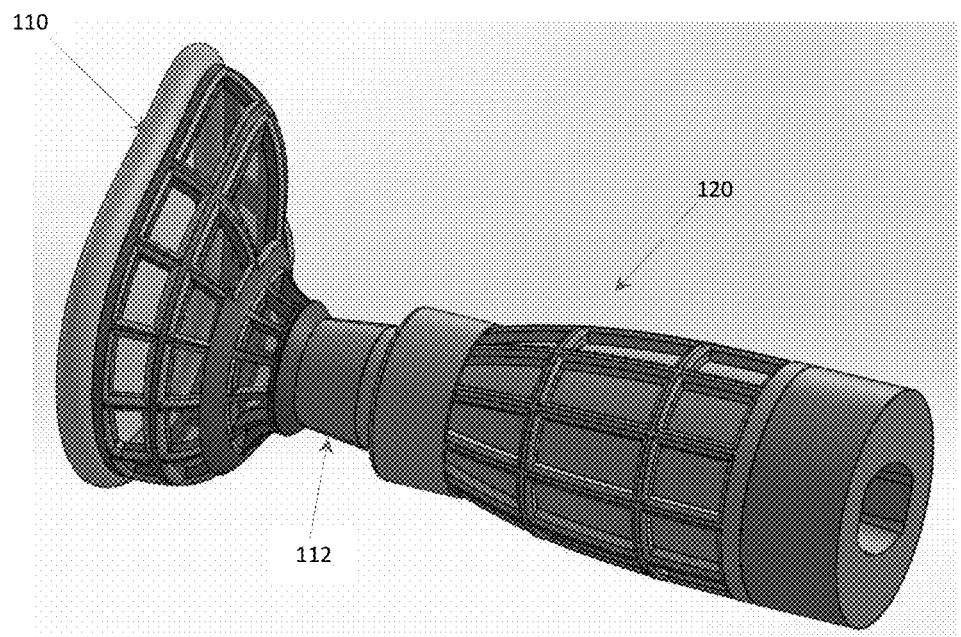
FIG. 10A is a perspective view of a collapsible spacer used in combination with a collapsible face mask.
Figure 10B:
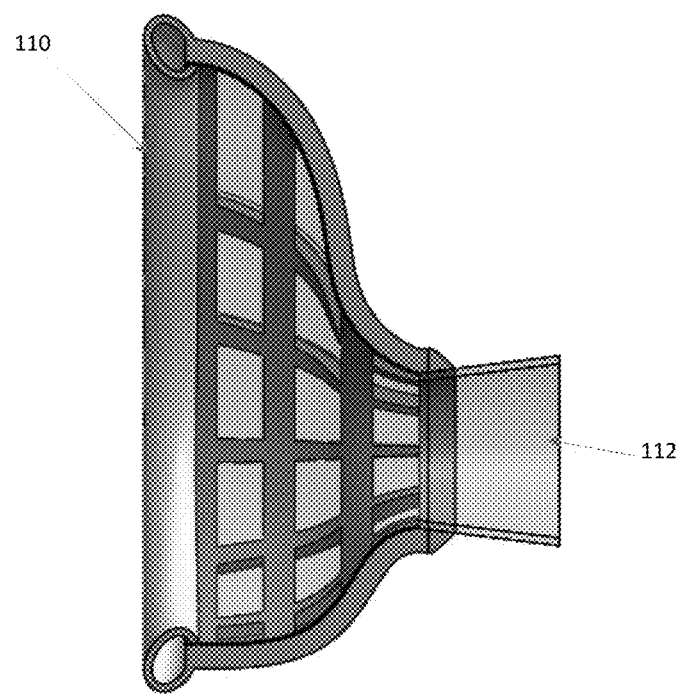
FIG. 10B is a side view of the collapsible face mask of FIG. 10A.

FIG. 8C shows the inflation system 800 that can be used with respect to the inflatable spacers 80 of FIGS. 8A and 8B. The inflation system 800 comprises a mechanical, electrical or any other type of pump 801, a one-way valve 803 and an outlet or vent valve 805. The pump 801 has one way valve 803 to allow the air in but not out. The Inflation system 800 can have a separate valve such as for example the vent valve 805 to let the air out if the spacer 80 needs to be deflated. The spacer 80 can be filled with air of any other fluid, by blowing the fluid inside the inflatable structure 81, 88 and closing the inlet 7 by the cap. A fan, blower, or pump 801 can be used to inflate the spacer 80. The inner wall 86 and the outer wall 87 can have necessary porosity to let the air out and automatically deflate the spacer after some time avoiding the need of a vent valve 805. In addition, the porosity of the inner wall 86 may help the formation of an aerosol of smaller size and prevent impaction and sedimentation and improve the efficacy of the drug delivery. The inflatable spacer 80 can be integrated with solid components (flexible, foldable, retractable, slidable, etc.) similar to the one explained herein above for better preserving the shape of the spacer. In one implementation, the inflatable spacer 80 can be self-inflating similar to the camping mattresses. An air absorbing material can be used inside the airtight (partially or completely) inflatable structure to suck the air in for inflation. It can be deflated by applying pressure on the inflatable structure to push the air out and deflate the spacer 80.

FIG. 9A illustrates another embodiment of a foldable spacer 90. The body of the spacer 90 comprises a series of rigid elements 91 which are connected by a flexible string 93 such as an elastic or rubber band. The other elements of this spacer 90 are similar to the elements described herein above with respect to FIGS. 1-8.

FIG. 9B shows the above mentioned spacer 90 in its collapsed position.

FIGS. 10A and 10B show an example embodiment of expandable, compressible, inflatable or foldable face mask 110 to be used with any design of the spacers/valved holding chambers described herein above. Similar to the spacers described herein above the face mask 110 can also be designed and configured to be collapsible, compressible, foldable or inflatable. The face mask 110 will retain the original shape when in its expanded position. The valve 112 of the spacer 120 can also be made collapsible, compressible, foldable or inflatable to help reducing the size of the spacer when it is compressed. An example of this face mask can be a compressible caged-like structure made of foam or any other compressible material. Another example is the face mask 110 with a caged shape inflatable body structure integrated with a flexible membrane body as described herein above with respect to FIG. 8.

In one implementation of the spacer, a combination of a retractable outer wall, similar to a telescopic structure or an origami design with a desired shape, or other similar structures, and an internal and/or external cover e.g. thin layer made of flexible (can be stretchable) material) can be used. The outer body is similar to an exoskeleton and the inner layer is similar to a skin to preserve the smoothness of the body. The inner body doesn't need to fill all the irregularities of the structure. Instead, it can be design to be attached only to those points and surfaces to ensure the irregularities are masked. The above mentioned flexible/stretchable layer can also be used as a cover for the retractable structure.

In one aspect of the spacer, the box/casing of the inhaler can be designed in a way to serve as the chamber or part of the structure of the spacer. Similar to the previous design an inner layer can be integrated with the box to ensure the smooth surface after the structure is expanded.

In one implementation of the design a rib structure similar to a foldable rib can be used to shape a flexible material.

In one implementation of the spacer, the rib can be made of smart materials similar to shape memory alloy. The spacer can be deformed into any shape and upon exposing to a temperature source or electric current it goes to its natural shape and form the spacer.

The invention claimed is:

1. A collapsible spacer to be used with an inhaler to deliver medication to a user, the spacer comprising:
    an outlet port adapted to be brought in communication with an oral cavity of the user; and
    a body having a first rigid end connected to the outlet port, a second rigid end configured to be connectable to the inhaler and a wall extending between the first end and the second end, the wall comprising a collapsible body structure forming an outer wall of the body, the collapsible body structure shaped as a cage and comprising a frame and a plurality of windows defined by the frame, and an elastic membrane attached to a bottom of the frame of the collapsible body structure at least at two points, the elastic membrane covering the plurality of windows and forming an inner wall of the body,
    wherein when the spacer is in an extended position the frame of the collapsible body structure has sufficient rigidity to keep a predetermined shape and integrity of the spacer and the elastic membrane is entirely stretched defining a smooth inner wall of the spacer, and wherein when the spacer is in a collapsed position the frame of the collapsible body structure collapses to a smaller size and the elastic membrane folds therein.

2. The collapsible spacer of claim 1, wherein the frame is made of a foam material, the elastic membrane being attached to the frame along its entire bottom.

3. The collapsible spacer of claim 1, wherein the frame comprises a network of interconnected inflatable tubes with an inner cavity and further comprising an inflatable system having a pump with a valve, the frame of the collapsible body structure having an inlet port as a communication port with the inner cavity of the frame, the inlet port having a removable cap, a portion of the inflatable system being insertable into the inlet port when the cap is removed to inflate the frame of the collapsible body structure when the spacer is in the extended position.

4. The collapsible spacer of claim 3, wherein the inflatable system further comprises a vent to deflate the frame of the collapsible body structure when the spacer is in the collapsed position.

5. The collapsible spacer of claim 1, further comprising a collapsible face mask attached at the outlet port of the spacer, the face mask having a collapsible outside wall and an elastic inner wall.

6. A method of delivering a medication to a user, the method comprising:
    connecting the collapsible spacer of claim 1 to an exit port of the inhaler;
    erecting the collapsible spacer to its extended position;
    actuating the inhaler so that the medication flows through the exit port into the spacer; and
    inhaling the medication in the spacer through the outlet port.

7. The collapsible spacer of claim 1, wherein the collapsible body structure is made of a combination of an elastic and non-elastic material.

8. An inhaler-based delivery system, the system comprising:
    an inhaler configured to discharge an aerosolized medication, the inhaler having an exit port;
    a collapsible spacer having an outlet port and a body having a first rigid end connected to the outlet port, a second rigid end connectable to the exit port of the inhaler and a wall extending between the first rigid end and the second rigid end, the wall comprising a collapsible body structure shaped as a cage having a frame and a plurality of windows and an elastic membrane attached to at least portion of a bottom frame, the elastic membrane covering the plurality of windows; and
    a connector configured to connect the spacer to the inhaler.

9. The inhaler-based delivery system of claim 8, further comprising a collapsible face mask attached at the outlet port of the spacer, the face mask having a collapsible outside wall and an elastic inner wall.

10. An inhaler-based delivery kit, the kit comprising:
    a package comprising:
        an inhaler with an exit port and containing a substance for delivery; and
        a collapsible spacer configured to be attachable to the exit port of the inhaler when the inhaler is in use, the collapsible spacer comprising a collapsible body structure shaped as a cage having a frame and a plurality of windows and an elastic membrane attached to at least a portion of a bottom of the frame, and the elastic membrane covering the plurality of windows.

* * * * *